(12) United States Patent
Reading et al.

(10) Patent No.: US 7,366,704 B2
(45) Date of Patent: Apr. 29, 2008

(54) SYSTEM AND METHOD FOR DECONVOLUTING THE EFFECT OF TOPOGRAPHY ON SCANNING PROBE MICROSCOPY MEASUREMENTS

(75) Inventors: Michael Reading, Leicester (GB); Duncan M. Price, Loughborough (GB)

(73) Assignee: Waters Investments, Limited, New Castle, DE (US)

( * ) Notice: Subject to any disclaimer, the term of this patent is extended or adjusted under 35 U.S.C. 154(b) by 1088 days.

(21) Appl. No.: 10/180,496

(22) Filed: Jun. 27, 2002

(65) Prior Publication Data

US 2003/0004905 A1    Jan. 2, 2003

Related U.S. Application Data

(60) Provisional application No. 60/301,129, filed on Jun. 28, 2001.

(51) Int. Cl.
| | |
|---|---|
| G06E 1/00 | (2006.01) |
| G06E 3/00 | (2006.01) |
| G06F 15/18 | (2006.01) |
| G06G 7/00 | (2006.01) |

(52) U.S. Cl. ............................. 706/16; 706/15; 706/26
(58) Field of Classification Search .................. 706/16, 706/26, 15
See application file for complete search history.

(56) References Cited

U.S. PATENT DOCUMENTS 6,095,679 A    8/2000  Hammiche et al.
6,260,997 B1   7/2001  Claybourn et al.
6,405,137 B1   6/2002  Reading (Continued)

FOREIGN PATENT DOCUMENTS

EP    WO9940417    * 12/1999

(Continued)

OTHER PUBLICATIONS

D. Price et al. "New Adventures in Thermal Analysis" Journal of Thermal Analysis and Calorimetry, vol. 60 (2000).

(Continued)

*Primary Examiner*—Joseph P Hirl
(74) *Attorney, Agent, or Firm*—Paul Hastings Janofsky & Walker, LLP

(57) ABSTRACT

A method for using a neural network to deconvolute the effects due to surface topography from the effects due to the other physical property being measured in a scanning probe microscopy (SPM) or atomic force microscopy (AFM) image. In the case of a thermal SPM, the SPM probe is scanned across the surface of a sample having known uniform thermal properties, measuring both the surface topography and thermal properties of the sample. The data thus collected forms a training data set. Several training data sets can be collected, preferably on samples having different surface topographies. A neural network is applied to the training data sets, such that the neural network learns how to deconvolute the effects dues to surface topography from the effects dues to the variations in thermal properties of a sample.

36 Claims, 16 Drawing Sheets

U.S. PATENT DOCUMENTS

| | | |
|---|---|---|
| 6,491,425 B1 | 12/2002 | Hammiche et al. |
| 6,666,075 B2 * | 12/2003 | Mancevski et al. ............ 73/105 |
| 6,690,016 B1 * | 2/2004 | Watkins et al. .......... 250/341.7 |
| 2001/0001755 A1 * | 5/2001 | Sandhu et al. ................. 451/5 |
| 2001/0027018 A1 * | 10/2001 | Molnar ....................... 438/690 |
| 2002/0048531 A1 * | 4/2002 | Fonash et al. ............. 422/68.1 |
| 2002/0121131 A1 * | 9/2002 | Mancevski et al. ........... 73/105 |
| 2005/0074871 A1 * | 4/2005 | Albert et al. ............ 435/287.2 |

FOREIGN PATENT DOCUMENTS

| | | |
|---|---|---|
| WO | WO-99/40417 | 12/1999 |

OTHER PUBLICATIONS

D. Grandy et al. "Microthermal Characterization of Segmented Polyurethane Elastomers and a Polystyrene-Poly(methyl methacryalate) Polymer Blend Using Variable Temperature Pulsed Force Mode Atomic Force Microscopy" Macromolecules 2000 (33, 9348-9359).

H.M. Pollock and A. Hammiche, "Micro-thermal analysis: techniques and applications," J. Physics D: Applied Physics, 2001, vol. 34, pp. R23-R53.

* cited by examiner

= POSITION OF PROBE

TABLE I

| PROBE LOCATION | Z-AXIS DIFFERENCES GIVING TOPOGRAPHIC PARAMETERS | | | | | | | | MEASURED VALUE | KNOWN OR PREDICTED VALUE |
|---|---|---|---|---|---|---|---|---|---|---|
| | A-X | B-X | C-X | D-X | E-X | F-X | G-X | H-X | | |
| 1,1 | 1 | 3 | 0 | 3 | 1 | 2 | 1 | 3 | 8 | 9 |
| 1,2 | 2 | 3 | 4 | 2 | 6 | 1 | 2 | 2 | 5 | 9 |
| 1,3 | 4 | 6 | 4 | 1 | 4 | 4 | 3 | 1 | 11 | 9 |

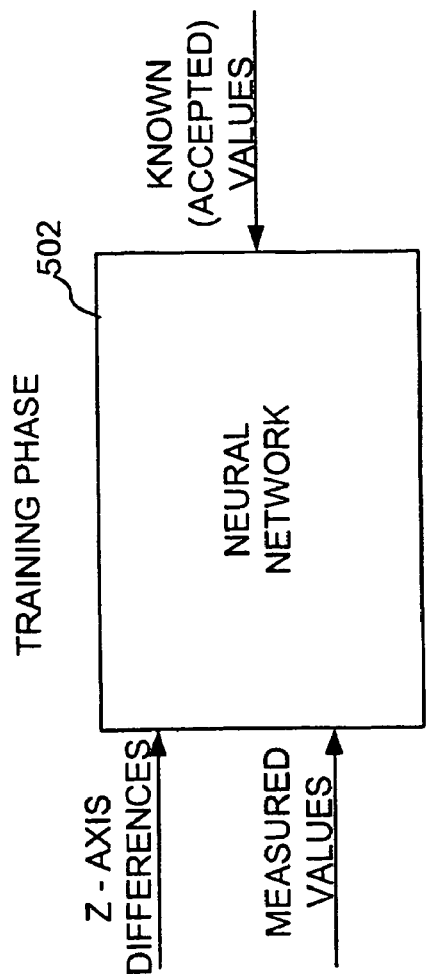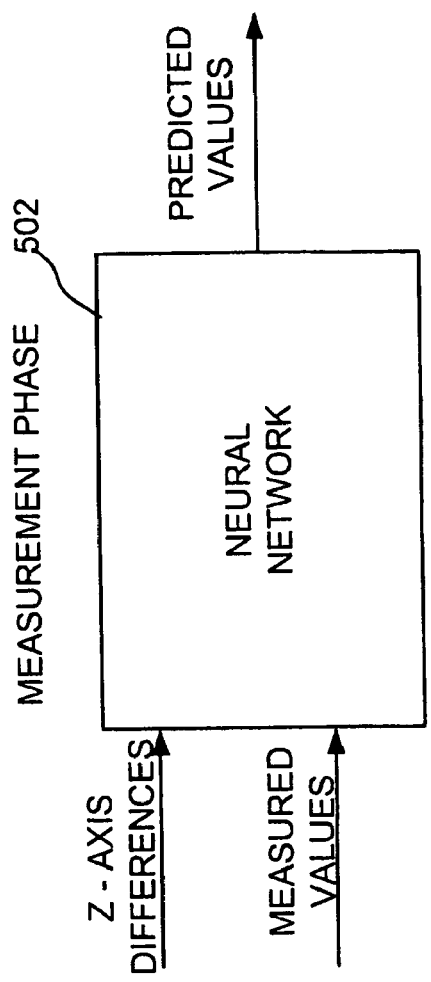

ILLUSTRATION OF DECONVOLUTION OF TOPOGRAPHIC EFFECTS

ILLUSTRATION OF DECONVOLUTION OF TOPOGRAPHIC EFFECTS

SYSTEM AND METHOD FOR DECONVOLUTING THE EFFECT OF TOPOGRAPHY ON SCANNING PROBE MICROSCOPY MEASUREMENTS

The present application claims the benefit of U.S. Provisional Application 60/301,129, filed Jun. 28, 2001, which is hereby incorporated by reference herein in its entirety.

BACKGROUND

1. Field of the Invention

The present invention relates generally to scanning probe microscopy (SPM), and more specifically to systems and methods for deconvoluting the effects of surface topography from the effects due to the other physical properties of the surface being scanned.

2. Background of the Invention

U.S. Pat. Nos. 6,095,679, 6,260,997 and 6,405,137 and U.S. patent application Ser. No. 09/584,396 filed Jun. 1, 2000, are incorporated herein by reference in their entirety. These patents and this patent application describe thermal scanning probe microscopes, in which the thermal properties of a sample can be imaged by scanning a thermal probe over the surface of the sample, and methods for obtaining images representative of the thermal properties of the sample. Further background information describing the state of the art is disclosed in the article, "New Adventures in Thermal Analysis," by D. M. Price, M. Reading, A. Hammiche and H. M. Pollock, Journal of Thermal Analysis and Calorimetry, Vol. 60 (2000) (the "New Adventures" article), which is also incorporated by reference herein in its entirety. The New Adventures article describes the combination of scanning probe microscopes (also referred to as atomic force microscopes) with thermal analysis material characterization techniques to obtain images of a surface of a sample according to variations in the sample's thermal conductivity or thermal expansivity.

FIG. 1(a) is a schematic diagram of a scanning probe or atomic force microscope. FIG. 1(a) shows a sample 10 having a non-smooth surface 11. A probe tip 12 is held against surface 11 by a cantilever 13 extending from a support 14. A laser 15 directs a laser beam 16 at a mirror 17 attached to the end of the cantilever above the probe tip. The beam reflects from the mirror onto a detector 18. The position of the reflected beam on detector 18 (e.g., areas 1 and 2 on detector 18) is used as a measure of the vertical position of probe tip 12, and hence as a measure of the surface topography of the sample. Probe tip 12 is scanned across the sample in an x-y array as the vertical position is measured, thus providing data for computing a topographical image of the sample surface.

If the material is to be characterized according to its thermal conductivity, the probe tip of a conventional atomic force microscope is replaced by, for example, an ultra miniature resistive heater that also serves as a temperature sensor. Such a probe is illustrated schematically in FIG. 1(b). As shown in FIG. 1(b), preferably the probe comprises Wollaston wires 21 extending from a ceramic insulator 22. This probe can be fabricated, for example, from Wollaston process wire which consists of a thin platinum core (e.g., about 5 microns in diameter) surrounded by a thick silver sheath (e.g., about 75 microns in diameter). The wire is formed into a loop and attached to a support structure to produce a cantilever. The silver at the end of the loop is etched away, exposing a platinum core. The platinum core is a fine platinum filament 23 that is bent down to form a probe tip 24.

When current is passed through the probe, heating occurs primarily in the exposed platinum filament 23. A small silicon wafer cemented across the arms of the Wollaston wire cantilever next to the bent platinum filament 23 is used as the mirror 17 that provides position information via an optical feedback circuit, as described above. The heat lost from the probe is monitored by operating the probe in a constant temperature mode, whereby the power required to maintain the tip at a predetermined constant temperature is measured during data acquisition. Image contrast is obtained because regions of high apparent thermal conductivity require greater power to maintain the probe at the predetermined constant temperature compared to regions of lower apparent thermal conductivity. An alternative is to supply the tip with a constant current and the changes in temperature of the tip can provide equivalent maps of thermal properties.

If the material is to be characterized according to its thermal expansivity, the same probe is used, and the z-axis deflection of the probe is monitored as a function of the probe temperature, while the probe temperature is ramped as in conventional thermal analysis. Also, simultaneous calorimetric information regarding the nature of transitions in the sample can be obtained by measuring the power required to make the probe follow a given temperature program and simultaneously measuring and comparing to the power required to make a reference probe isolated from the sample (e.g., on a reference material) follow the same temperature program, calorimetric information. Alternatively, an AC temperature modulation can be applied during the heating ramp, and the changes in power required to keep the modulation amplitude constant can be measured, thus providing a microscopic analog to modulated temperature differential scanning calorimetry. Although this technique is not currently quantitative, measuring the temperature of a transition is, in many cases, sufficient to identify a phase in the sample.

Another imaging mode can be obtained by localized AC heating of the tip which causes the surface to expand and contract according to its thermal expansivity. This can be detected using a lock-in amplifier to generate an image whose contrast derives from the apparent differences in thermal expansivity of the surface components.

In the above-described cases and as a general rule, in all scanning probe microscopy measurements, the topography of the surface may influence the measurement being made. For example, if the thermal conductivity of a sample is being mapped, when the tip of the probe descends into a depression on the surface, the area of contact between the tip and the sample increases, resulting in an apparent increase in the local thermal conductivity. The opposite is true when the probe meets an asperity.

FIG. 2 illustrates the effect of topography on the apparent thermal conductivity of a sample. The schematic drawings on the left of FIG. 2 represent the surface topography of the sample, and its thermal conductivity (the dark gray represents the higher conductivity phase and the light gray represents the lower conductivity phase). The plots on the right of FIG. 2 illustrate the apparent thermal conductivity of the sample, as it would be measured using prior art techniques. As can be seen, whereas the plots corresponding to the smooth surfaces (plots 1 and 3) accurately represent the thermal conductivities of the sample, the plots corresponding to the rough samples (plots 2 and 4) show a false peak (due to the depression on the left side of the sample) and a false valley (due to an asperity on the right side of the sample). Clearly the effects of topography complicates the interpretation of the thermal image because the information actually being sought is the disposition of the phases having different thermal conductivities within the sample.

The images obtained using the thermal scanning probe microscope can be further enhanced by fitting Gaussian peaks to the distribution of pixel intensity in the histograms. This technique is described in the article "Microthermal Characterization of Segmented Polyurethane Elastomers and a Polystyrene—Poly(methyl methacryalate) Polymer Blend Using Variable Temperature Pulsed Force Mode Atomic Force Microscopy," D. B. Grandy, D. J. Hourston, D. M. Price, M. Reading, G. Goulart Silva, M. Song and P. A. Sykes (published in *Macromolecules* 2000, 33, 9348-9359), which is incorporated by reference herein. Briefly, the technique comprises (1) obtaining a thermal scanning microscope image; (2) deriving a histogram distribution of the number of pixels vs. intensity for the image; (3) noting that the histogram appears to show two or more peaks; (4) fitting Gaussian distributions to the peaks in the histogram; and (5) using the intersection between the fitted peaks as a "decision boundary" to re-color the original image.

This process is illustrated in FIGS. 3(a) to (3(c). FIG. 3(a) shows a thermal image of a paracetamol tablet. A linear gray scale between 1.55 mW and 2.075 mW is used to denote the z-axis. FIG. 3(b) is a histogram of the distributions of pixels versus intensity for the image of FIG. 3(a). The raw data shows that there are two peaks in the histogram, one relatively narrow peak a little above 1.625 mW, and a broader peak centered roughly at 1.775 mW. This data has been fitted to two Gaussian distributions, shown in FIG. 3(b) as gray lines. (The narrow peak corresponds to the drug phase, and the broader peak corresponds to an excipient.) The intersection between the two peaks occurs at 1.667 mW. Thus 1.667 mW is the "decision boundary" as to whether a pixel should be assigned to one phase or the other. FIG. 3(c) is a black and white version of the image of FIG. 3(a), obtained by assigning black to all pixels having a value below 1.667 mW, and white to all pixels having a value above 1.667 mW. FIG. 3(c) shows the distribution of the two phases more clearly than does FIG. 3(a).

A more sophisticated approach assigns a probability of the pixel belong to one state or the other. In that case, instead of having purely black or purely white pixels, the pixels are assigned a color on a gray scale ranging from white to black. For example, the gray scale level plot shown in FIG. 4(a) can be used to assign the pixels of the image of FIG. 3(a) to a gray scale level that depends on the probability of the pixel belonging to one phase or the other. FIG. 4(b) shows the result of this approach. The image in FIG. 4(b) is not as dramatic as the image of FIG. 3(c), but is probably more realistic. For example, the gray areas might represent pixels having contributions from both phases, possibly due to the subsurface structure of the sample.

SUMMARY OF THE INVENTION

The present invention solves the problem of the effects of topography on apparent thermal conductivity by deconvoluting the effects due to the surface topography from the effects due to the other physical property (thermal conductivity in the examples described herein) being measured. In one embodiment of the present invention, the deconvolution is performed using a neural network. The image can be considered as a grid of points or pixels. The probe is moved over the sample, and measurements are made at each point of both the apparent thermal conductivity of the sample and the topography of the sample. The neural network is trained using a data set obtained from known calibrants.

BRIEF DESCRIPTION OF THE DRAWINGS

FIG. 5(a) is a table providing exemplary z-axis topographical differences between pixels and corresponding measured and known/predicted conductivity values.

FIG. 5(b) is a schematic diagram for training a neural network according to a neural network embodiment of the present invention.

FIG. 5(c) is a schematic diagram for using a neural network in a measurement phase according to a neural network embodiment of the present invention.

DETAILED DESCRIPTION OF THE INVENTION

The present invention is described in terms of a thermal SPM. However, in principle, exactly the same approach can be adapted for analyzing data or improving the quality of images obtained using at any SPM mode.

The present invention solves the problem of the effects of topography on apparent thermal conductivity by deconvoluting the effects due to the surface topography from the effects due to the other physical property (thermal conductivity in the examples described herein) being measured. In one embodiment of the present invention, the deconvolution is performed using a neural network. The image can be considered as a grid of points or pixels, as shown in FIG. 5.

The probe is moved over the sample, and measurements are made at each point of both the apparent thermal conductivity of the sample and the topography of the sample.

FIG. 5(a) is an exemplary table showing the local topography for each probe location.

Figure 1A:
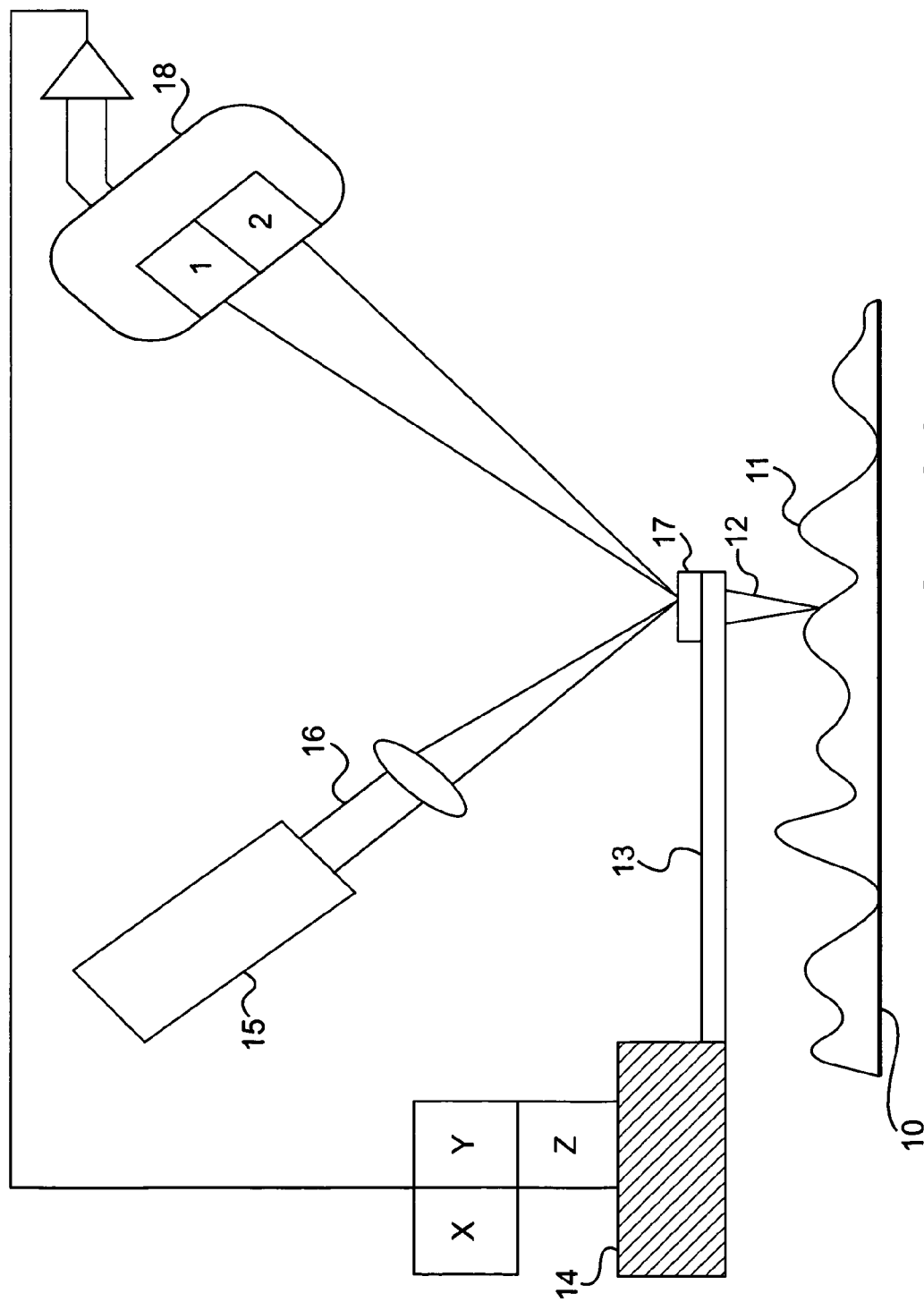
FIG. 1(a) is a schematic diagram illustrating a scanning probe microscope (SPM).
Figure 1B:
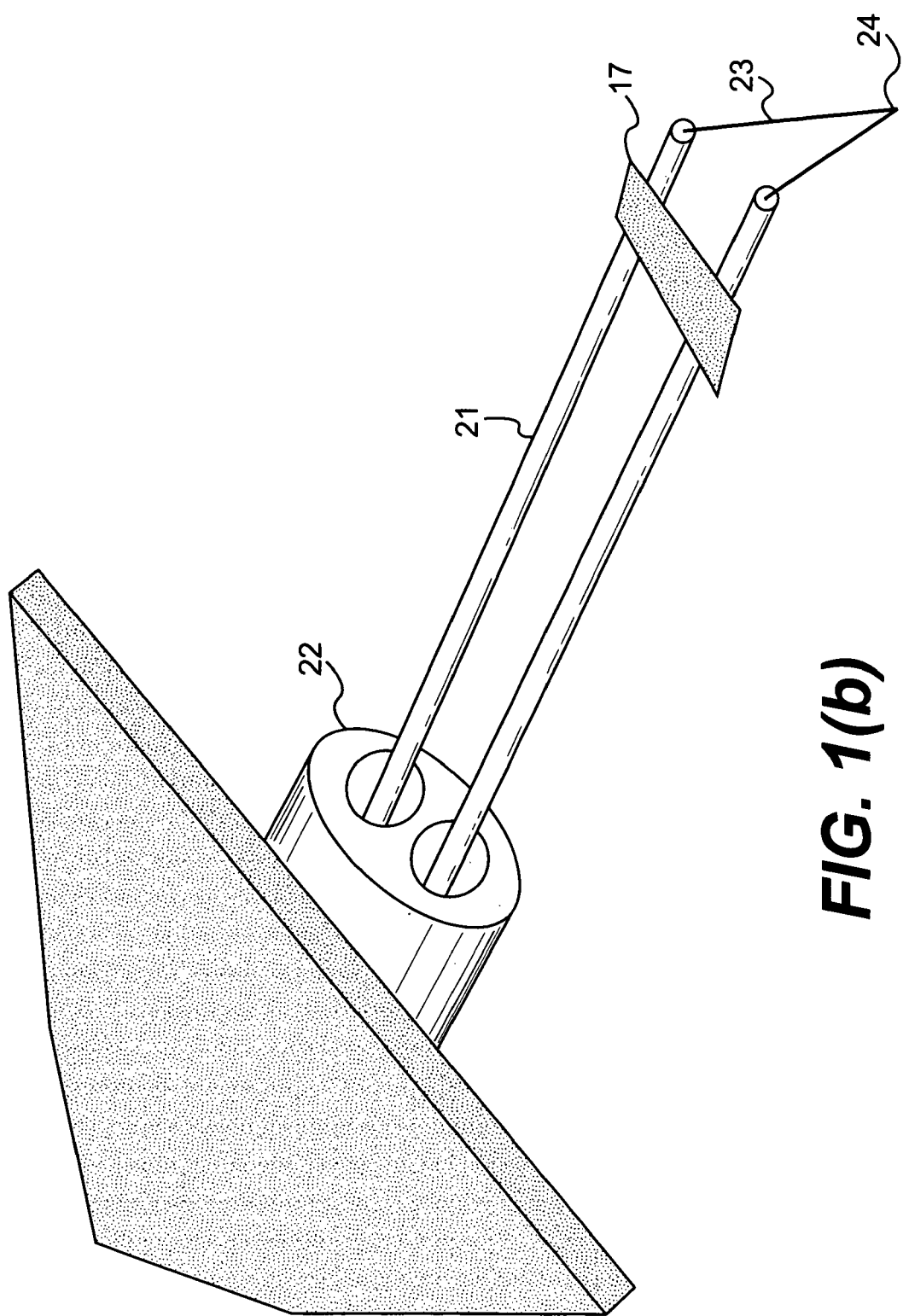
FIG. 1(b) is a schematic diagram illustrating a thermal probe.
Figure 2:
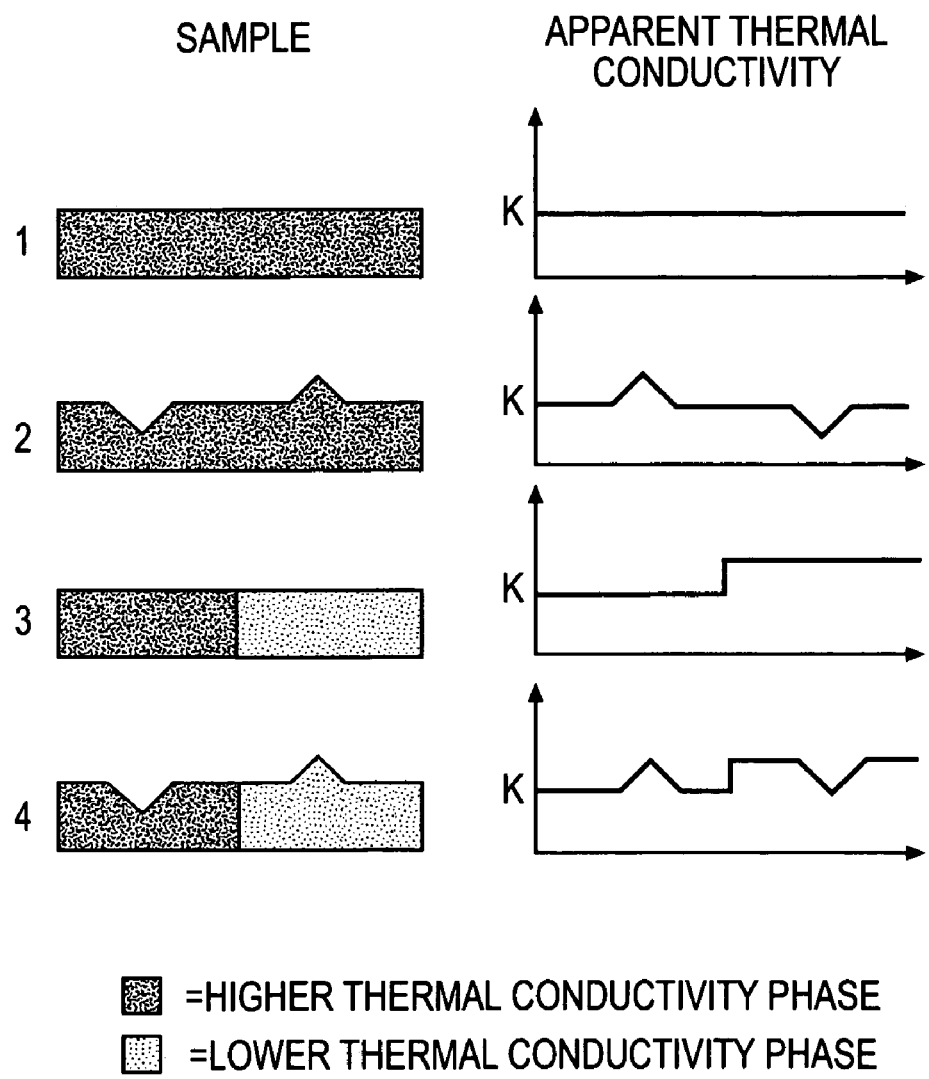
FIG. 2 illustrates the effect of topography on apparent thermal conductivity.
Figure 3A:
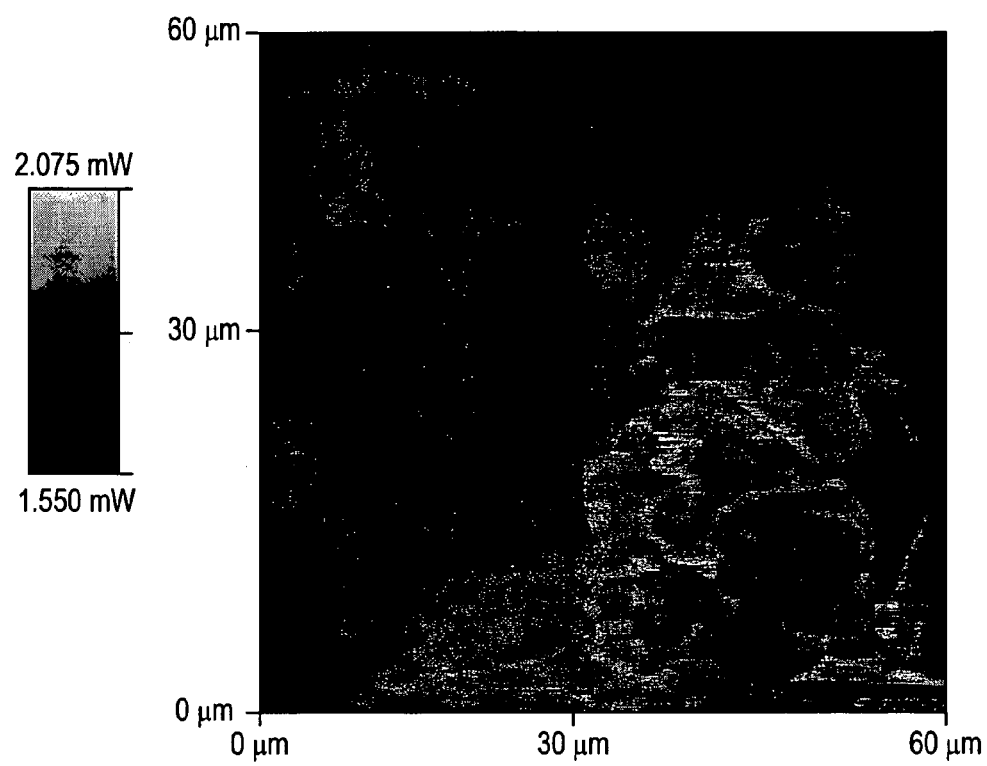
FIG. 3(a) is a gray scale thermal SPM image of a paracetamol tablet, obtained with a probe temperature of 50° C.
Figure 3B:
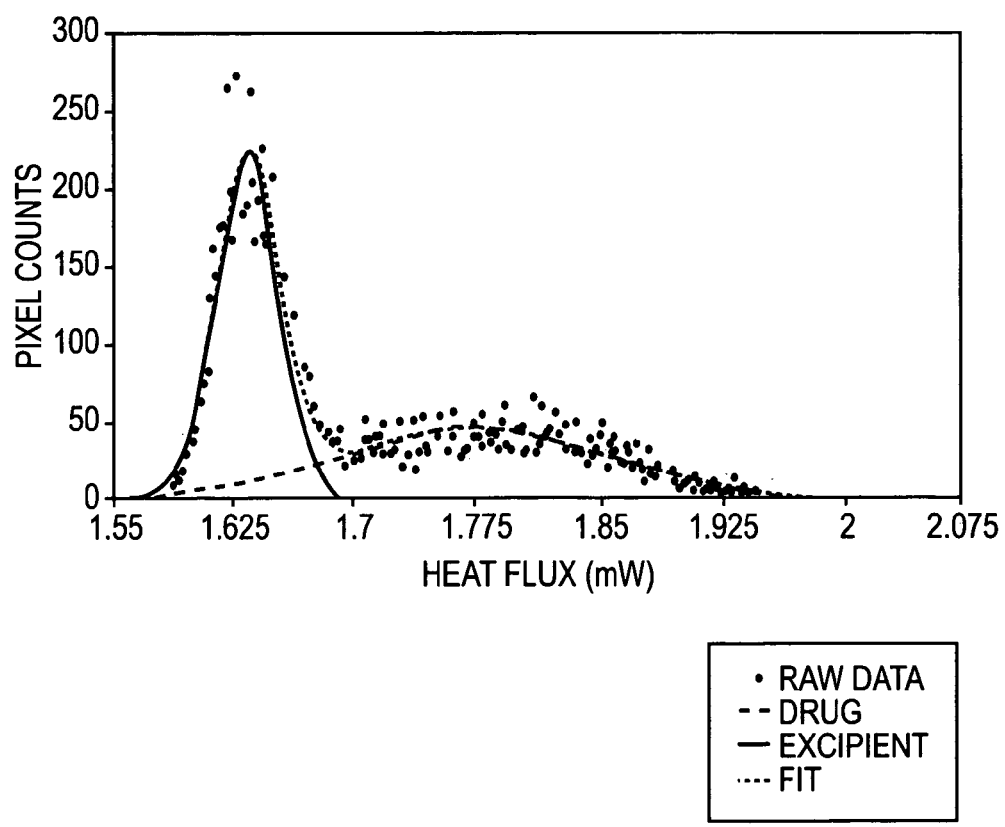
FIG. 3(b) is a histogram of the distribution of pixels vs. intensity for the image of FIG. 3(a).
Figure 3C:
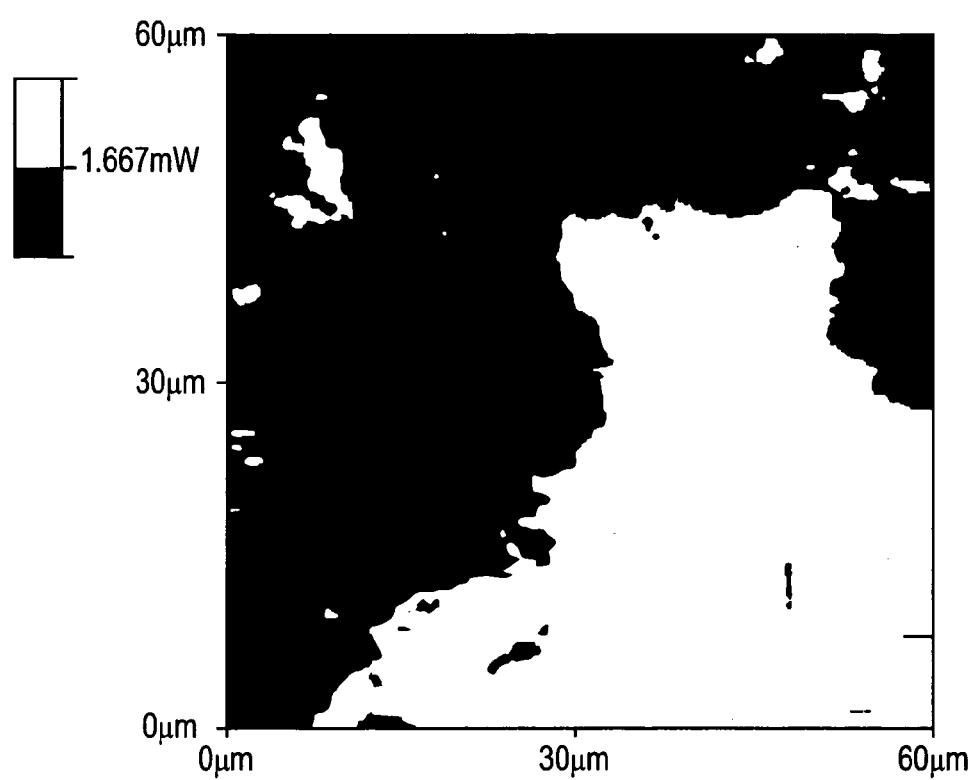
FIG. 3(c) is an enhanced black/white version of the thermal SPM image of FIG. 3(a).
Figure 4A:
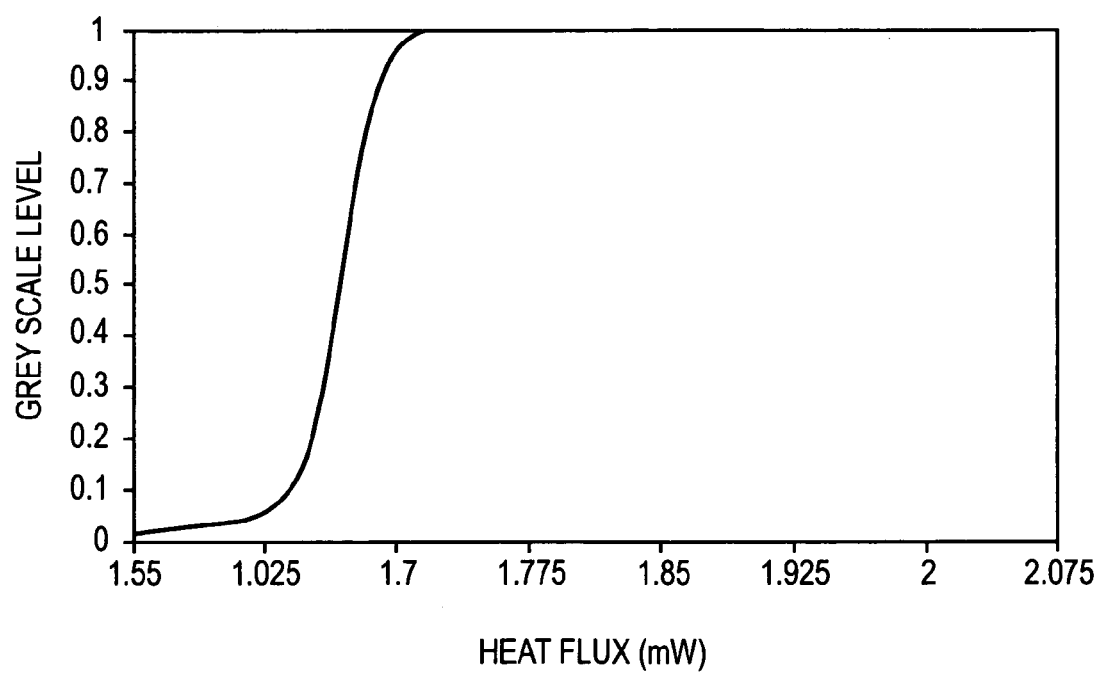
FIG. 4(a) is an exemplary gray scale level plot, wherein the gray scale level depends on the probability of the pixel belonging to one phase or the other.
Figure 4B:
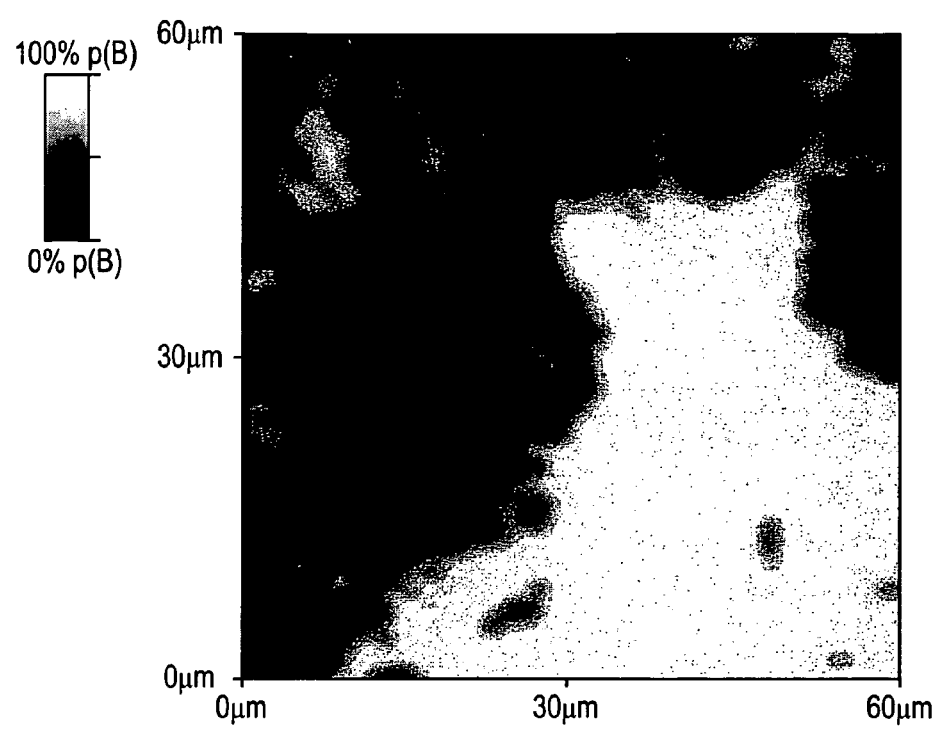
FIG. 4(b) is an enhanced gray scale version of the thermal SPM image of FIG. 3(a).
Figure 5:
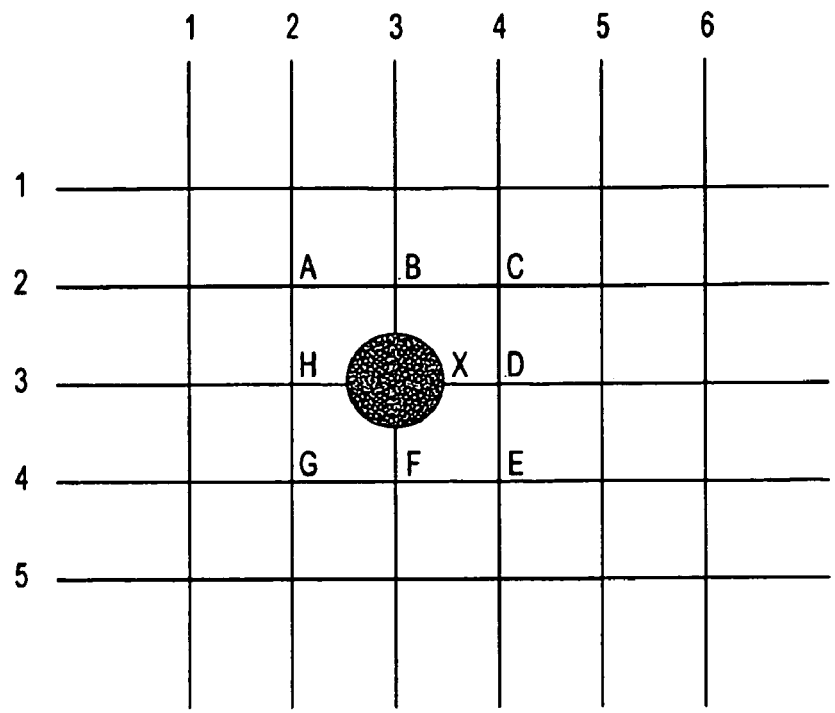
FIG. 5 is a schematic illustration of a probe on a grid of points.

For each point or pixel, the local topography is characterized by subtracting its height from the heights of its eight "nearest neighbor" surrounding points a, b, c, d, e, f, g and h, shown in FIG. 5.

The thermal conductivity of the sample at that position is also measured, and the measurement value is stored in the table. To provide training data for the neural network, measurements are made on materials of known thermal properties. In the simplest version, a set of calibrants is taken with surface topography that varies from the very smooth to the very rough. The approach that is illustrated in the FIG. 5 and the table in FIG. 5(a) relies on using in the training set the height differences between the pixel and its adjacent "nearest neighbor" pixels. In general, pixels further removed from the pixel could be included, and it would generally be preferable to do this, although in that case more time would be required to train a system using a neural network.

For all of these samples the "true" thermal measurement is the value obtained on the very smooth surface and stored in the table. For a completely smooth compositionally homogeneous sample the same thermal response should be measured at each point on the sample's surface. In practice, an average value from the smoothest available surface of the sample can sometimes be taken as the "true" value when a suitable set of calibrants is not available or insufficient time is available for calibration using these calibrants. From these samples (samples being used for calibration, with a surface topography that ranges from the very smooth to the very rough), a table of topographic parameters is obtained together with the apparent thermal conductivity measurement for a wide range of different topographies. In each case, the required value is given as the measurement on a smooth surface.

Preferably, a variety of different samples is used with different thermal properties (i.e., different values on the very smooth surface). For best results, the surface topography should vary from very smooth to rough, with different types of roughness, e.g., jagged, rounded or fractal roughness. Preferably, the roughness of the training set be similar to the roughness of the samples that are to be studied. At least two training runs must be made with each material, one with a very smooth surface, and one with a rough surface. Preferably, the rough surface should be at least as rough as the surface of the sample to be imaged. More than two training runs improve the quality and reliability of the results. This then forms the training set that the neural network uses to "learn" how to remove the effect of topography, to obtain the thermal conductivity that would have been obtained had the surface been very smooth. Suitable neural network software is available commercially, e.g., "BackPack Neural Network System" or "Pathfinder Neural Network System", available from Z Solutions, Inc., Roswell Road, Atlanta, Ga. 30328.

In a neural network-based embodiment of the present invention, a neural network processes input data to produce deconvoluted thermal conductivity data. In this sense, the neural network deconvolutes the thermal conductivity information from the topographic information. To use neural networks, they must be trained. FIG. 5(b) is a schematic diagram for training a neural network 502 in a training phase according to a neural network embodiment of the present invention. The training data set is stored in a table similar to that shown in FIG. 5(a). For the training phase, the last column of the table stores known (or accepted) values of thermal conductivity for the sample being used to train neural network 502.

In the training phase, z-axis differences for the nearest neighbor pixels to the pixel being analyzed (and other pixels further removed from the pixel being analyzed if desired) are input to the neural network. In addition, the measured value of thermal conductivity and the known (or accepted) value of thermal conductivity at the pixel being analyzed are input to the neural network. This process is performed for each data point in the training data set.

After neural network 502 has been trained, it can be used to analyzed measurement data obtained in a measurement phase as shown in FIG. 5(c). A table similar to that illustrated in FIG. 5(a) is created. In the measurement phase, the last column of the table is the predicted value of the thermal conductivity at the pixel being analyzed as output by neural network 502 in response to its inputs. The inputs to neural network 502 for the measurement phase are z-axis differences for the nearest neighbor pixels to the pixel being analyzed (and other pixels further removed from the pixel being analyzed if desired) and the measured value of thermal conductivity at that pixel being analyzed.

In some cases it is preferable to pre-process the data prior to applying it to neural network 502 in the training and/or measurement phase. In this case, any desired pre-processing of the data can be performed. Well known data pre-processing for use in neural network applications include data normalization and data transformation.

Figure 6A:
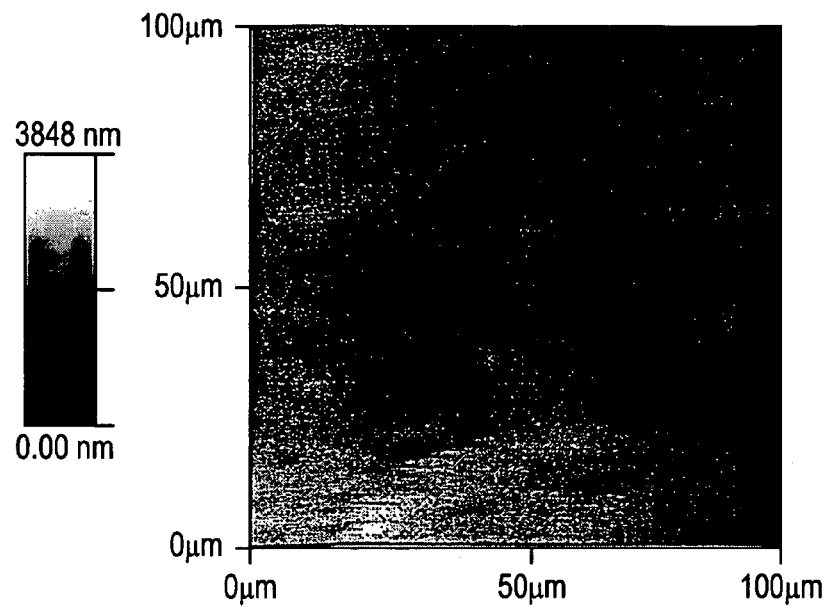
FIGS. 6(a)-6(d) are a series of micrographs ((a)-(d)) and histograms ((e) and (f)) illustrating the deconvolution of topographic effects.
Figure 6B:
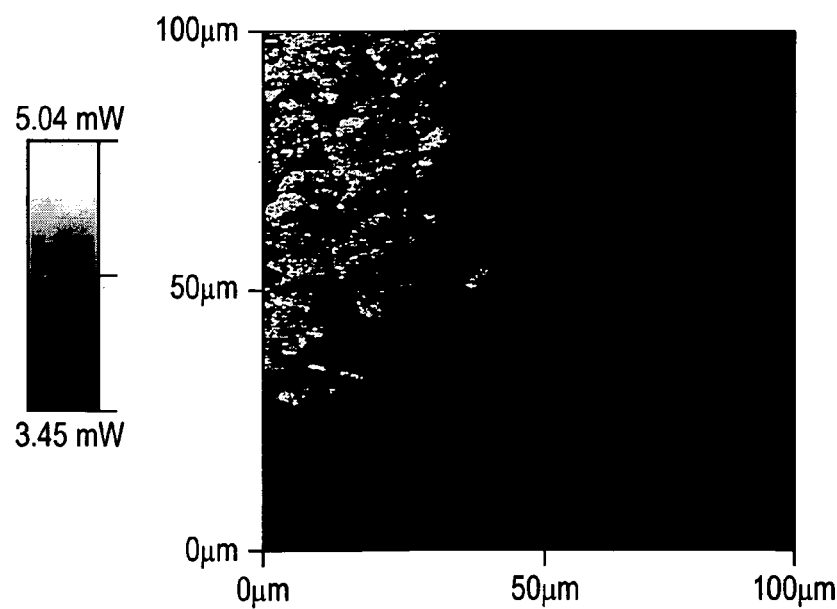
Figure 6C:
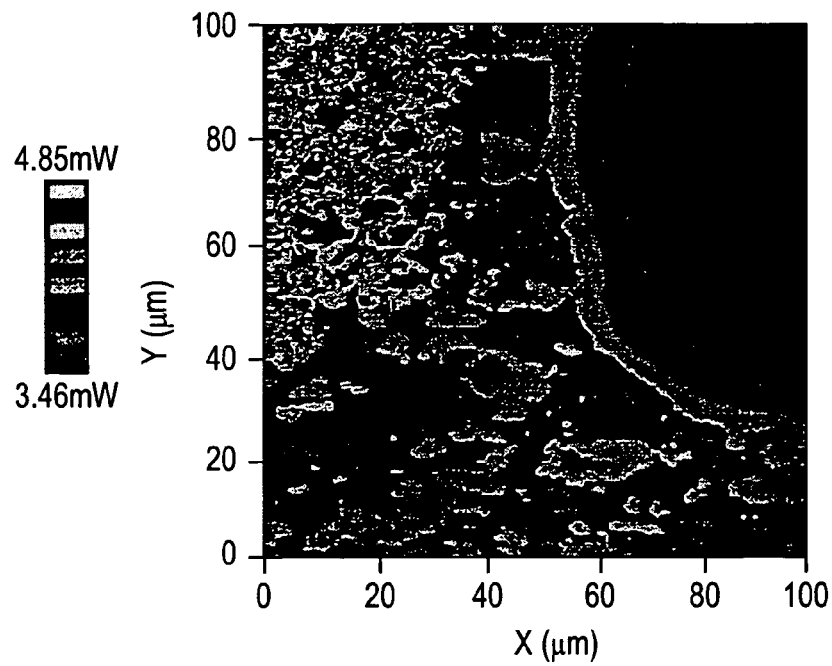
Figure 6D:
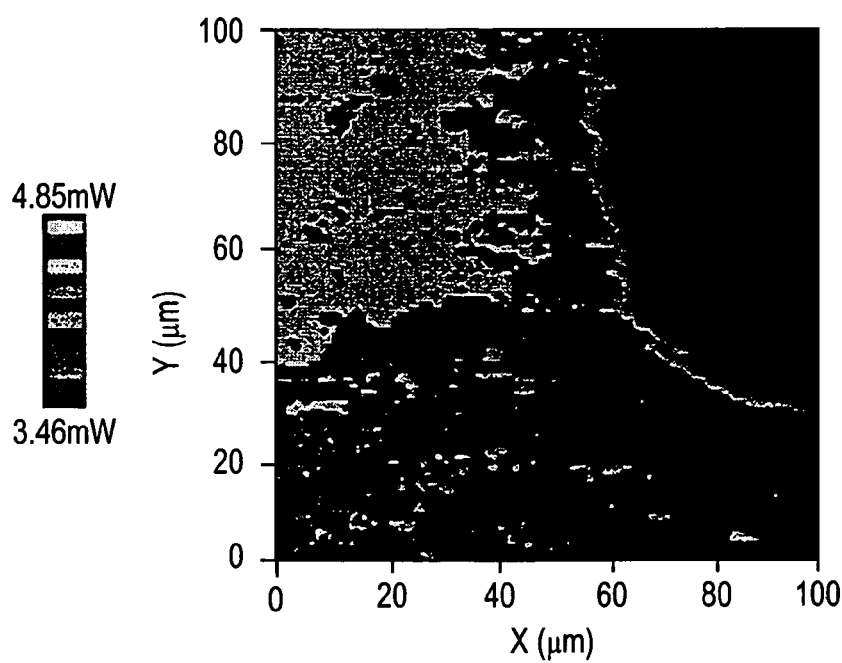

FIGS. 6(a)-6(f) illustrate the results obtained from applying the present invention to an inhomogeneous sample having a rough surface. The sample has three phases of materials, one material phase having a relatively low thermal conductivity, a second material phase having a relatively high thermal conductivity, and a third material phase having an intermediate thermal conductivity. The micrograph shown in FIG. 6(a) is a measurement of the topography of the sample. The micrographs shown in FIGS. 6(b) and 6(c) show the combined effects of the topography and the inhomogeneity in the thermal conductivity of the sample. The micrograph of FIG. 6(b) is based on the raw thermal data. The micrograph of FIG. 6(c) is based on the same raw thermal data as used in 6(b), but it uses a color scale to better illustrate the variations in the data. The micrograph shown in FIG. 6(d) illustrates the results of the present invention: it is similar to micrograph shown in FIG. 6(c), but the variations due to the surface topography have been substantially removed, by applying the neural network to remove the topographic effects from the image.

The sample comprises three different phases which can barely be discerned in the thermal image shown in FIG. 6(b). There is a dark phase at the top right, a bright phase at the top left and an intermediate phase at the bottom. Although the practiced eye can allow for the effects of topography to some extent to discriminate these phases, there is still a wide range of values obtained for the thermal measurement within each phase. In the image shown in FIG. 6(d), the results of applying the neural network are seen. Each phase has become significantly more homogeneous.

Figure 6E:
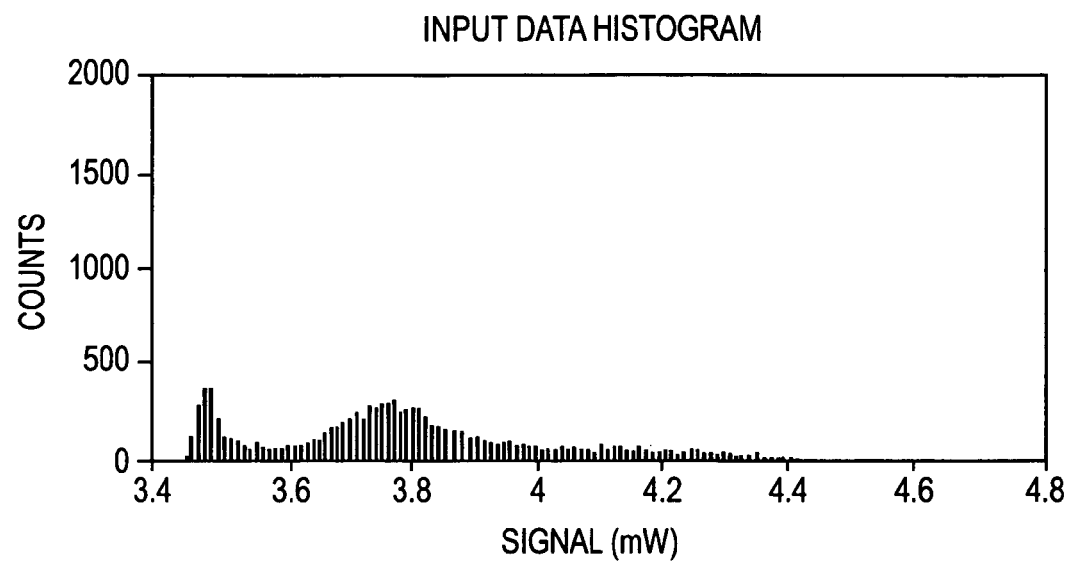
Figure 6F:
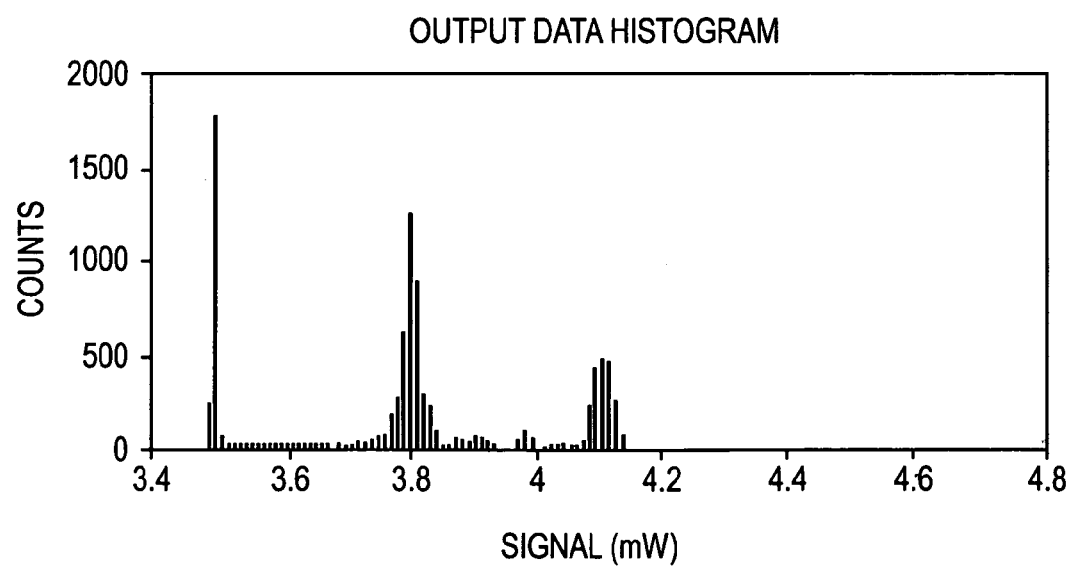

The histograms shown in FIGS. 6(e) and 6(f) were taken from the images shown in FIGS. 6(c) and 6(d), respectively. These histograms also illustrate the advantage of using the present invention. The peaks are dramatically sharpened with greater differentiation between them in the histogram of 6(f) than in the histogram of 6(e). FIG. 6 shows that the method of the present invention is very effective at deconvoluting (or separating) the effects due to the thermal conductivity of the sample from the effects due to the surface topography (or roughness) of the sample, and then compensating for the effect of topography so that interpretation of the image is simplified.

The images obtained using the present invention can be enhanced by fitting Gaussian peaks to the distribution of pixel intensity in the histograms, using the techniques described above. For example, Gaussian peaks could be fitted to the three main peaks in the histogram shown in FIG.

6f (the peaks at 3.5 mW, 3.8 mW and 4.2 mW). The intersections of the fitted Gaussian peaks could then be used to establish "decision boundaries" between the bright, intermediate and dark phases of the image, and the image could be re-colored accordingly, using, for example black, gray and white to produce a sharper image of the sample. Color images could also be produced, by assigning, for example, yellow to the bright phase, green to the intermediate phase, and blue to the dark phase. The more sophisticated approach to provide gray levels based on the probability of a particular pixel belonging to one or the other of the phases described above could also be used to allow, for example, for pixels having contributions from more than one phase.

Figure 7A:
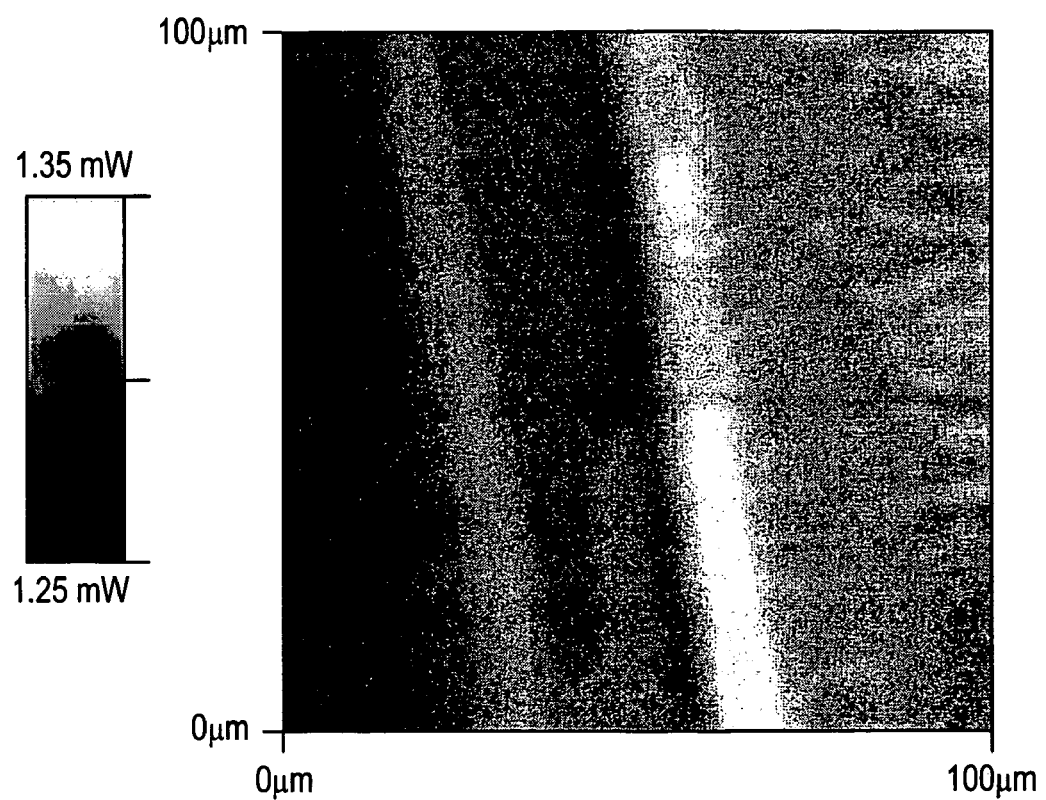
FIGS. 7(a)-7(c) are a series of micrographs illustrating the deconvolution of topographic effects from the physical properties of a sample.
Figure 7B:
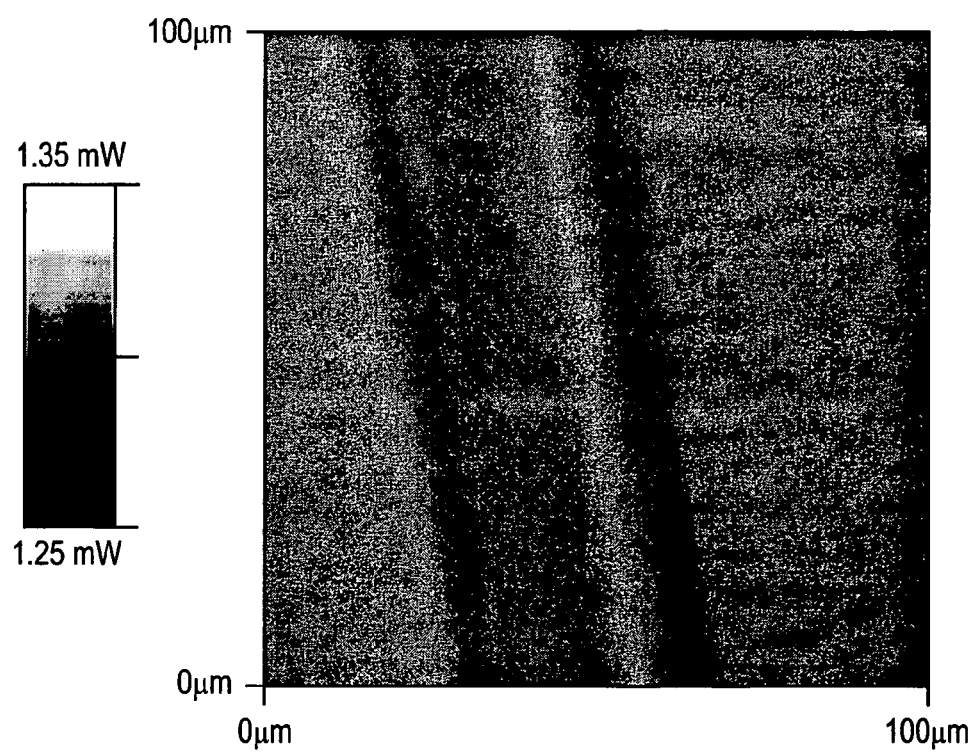
Figure 7C:
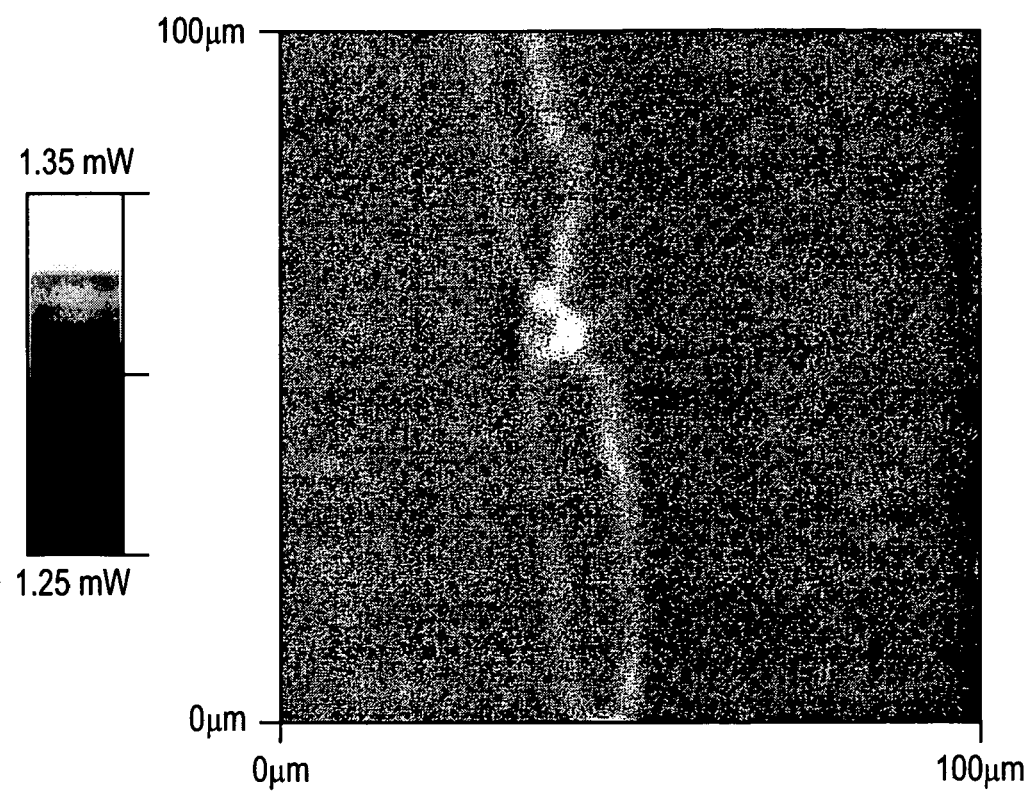

FIGS. 7(a)-7(c) show the results for a multilayer film made of, for the most part, different grades of polyethylene. The image in FIG. 7(a) shows the topography of the multilayer film, while the image in FIG. 7(b) shows the uncorrected relative thermal conductivity map. FIG. 7(b) apparently shows a number of different layers with different thermal conductivities. The image in FIG. 7(c) is a thermal conductivity image corrected using neural network according to the present invention. FIG. 7(c) is substantially more homogeneous than FIG. 7(b). This is the correct result for this sample, because the different grades of polyethylene have almost identical thermal conductivities. The remaining features shown in FIG. 7(c) may actually reflect in homogeneities in the sample, or may simply be due to imperfect or incomplete deconvolution. In the latter case, these features would disappear with a more extended training set, and/or by also taking into account in the training data not just the nearest pixels to each point but also pixels further removed from each point.

Further Embodiments of the Invention

Instead of a calibration set based on a series of standards, within a single image different areas could be selected that are clearly one phase so that a training set can be obtained to interpret the whole image, the average (or predicted or known) value of the signal being used for the training.

Because each probe is different, a master training set could be generated using a typical probe. A surface or a range of surfaces for a standard or standards (but a much smaller number than used in the master training set) could then be used for comparison of different probes in order to generate a neural network that corrects data for different probes shapes for subsequent input into the set trained on the master training set. This would reduce the time required to calibrate each probe.

It is known that the modulus of the material and the force applied can affect the contact area and thus apparent thermal properties. This could be inputted as a variable in the training set. This could then be measured through an indentation shear measurement made either simultaneously with the thermal measurement, or previous to or subsequent to the thermal measurement, with the same or a different probe.

In the above description the required value is the value obtained on a smooth surface. Another possibility is to calibrate the neural network to give a thermal property, e.g., thermal conductivity.

The above description related to thermal measurements. However, exactly the same procedure can be applied to any SPM measurement such as phase, pulsed force, force modulation, lateral force and other mechanical property imaging modes which exhibit similar artifacts due to the influence of topography (or other independently measured property) on the desired property image. It could also be applied to near field optical images. In cases where an intermittent contact mode is used, such as pulsed force, the neural network can be trained using the whole of the data set derived during a measurement cycle or some subset of these data.

The foregoing disclosure of the preferred embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible.

What we claim is:

1. A method for deconvoluting scanning probe microscopy images comprising:
   (a) using a physical property scanning probe microscope to obtain at least one topographic data set and at least one data set of an apparent physical property for a surface of a first sample, wherein said physical property of the first sample is known, and the topographic and apparent physical property data sets include data for at least one smooth and at least one rough topographic region of the surface of the first sample;
   (b) applying a neural network to the data set of said apparent physical property and the topographic data set of the first sample such that the neural network learns how to deconvolute the surface topographic effects from the effects of said physical property;
   (c) obtaining a data set of said apparent physical property and a topographic data set of a second sample using the physical property scanning probe microscope; and
   (d) using the neural network to deconvolute the surface topographic effects from the effects of said physical property on the data for the second sample to obtain a physical property data set of the second sample.

2. The method of claim 1, further comprising displaying, printing or plotting an image of the second sample based upon the physical property data set of the second sample obtained in step (d), wherein differences in color assigned to pixels that form the image of the sample indicate differences in the values of the physical property detected by the scanning probe microscope at corresponding points on the sample surface.

3. The method of claim 1, wherein the physical property is a thermal property and wherein the physical property scanning probe microscope is a thermal scanning probe microscope.

4. The method of claim 3, wherein the thermal property is thermal conductivity.

5. The method of claim 3, wherein the thermal property is thermal expansivity.

6. The method of claim 2, further comprising
   enhancing the image of the second sample by deriving a histogram distribution of the number of pixels having a given intensity value versus intensity for the image,
   fitting Gaussian distributions to at least two peaks in the histogram, each of which corresponds to a different phase on the surface of the second sample,
   using an intersection between fitted peaks as a decision boundary for determining whether a data value is indicative of a first phase or a second phase on the surface of the second sample, and re-coloring the image of the second sample by assigning pixels to said phases according to the decision boundary.

7. A method for creating an image reflecting a physical property of a surface of a sample from data obtained using a physical property scanning probe microscope, comprising:
(a) training a neural network to separate topographic effects from physical property effects on said data;
(b) scanning the surface of the sample using a physical property scanning probe microscope to obtain a topographic data set and an apparent physical property data set, the values of which reflect both physical property effects and topographic effects;
(c) applying the neural network to separate the topographic effects from the physical effects on the values of said apparent physical property data set;
(d) generating an image reflecting variations in the physical property of the surface of the sample.

8. The method of claim 7, wherein the physical property scanning probe microscope is a thermal scanning probe microscope.

9. The method of claim 8, wherein the physical property is thermal conductivity.

10. The method of claim 8, wherein the physical property is thermal expansivity.

11. The method of claim 7, further comprising fitting Gaussian distributions to peaks in a histogram distribution of the number of pixels having a given intensity value versus intensity for the image, and assigning values to the image pixels based upon the intersection between fitted peaks.

12. An apparatus for obtaining images reflecting a physical property of a surface of a sample comprising:
(a) a physical property scanning probe microscope; and
(b) a neural network,
wherein the neural network has been trained to separate topographic effects from physical property effects;
and wherein the neural network is used to separate the topographic effects from the physical effects to generate an image reflecting variations in the physical property of the surface of the sample.

13. The apparatus of claim 12, further comprising means for enhancing the image.

14. The apparatus of claim 12, wherein the physical property is a thermal property.

15. The apparatus of claim 14, wherein the thermal property is thermal conductivity.

16. The apparatus of claim 14, wherein the thermal property is thermal expansivity.

17. A thermal scanning probe microscope comprising:
(a) a cantilever arm;
(b) a thermal probe extending from said cantilever arm;
(c) means for scanning the thermal probe across the surface of a sample, and for recording thermal and topographic data as a function of position on the sample to obtain a data set reflecting thermal and topographic properties of the surface of the sample;
(d) a neural network for separating topographic effects from physical effects in the data set; and
(e) means for displaying an image reflecting the thermal properties of the sample.

18. The thermal scanning microscope of claim 17, wherein the thermal data is thermal conductivity data.

19. The thermal microscope of claim 18, wherein the thermal data is thermal expansivity data.

20. The thermal microscope of claim 19, further comprising means for enhancing the image reflecting the thermal properties of the sample.

21. A method for using a neural network to deconvolute the effect of topography from a thermal conductivity measurement made by a thermal scanning probe microscope comprising the steps of:
in a training phase of using the neural network:
(a) obtaining a sample of a material having a smooth surface;
(b) determining a true thermal conductivity of the sample;
(c) obtaining another sample of the material, the another sample having a rough surface;
(d) selecting a point on the rough surface;
(e) determining a local topography at the selected point;
(f) measuring a thermal conductivity at the selected point using said thermal scanning probe microscope; and
(g) storing the selected point, the local topography, the true thermal conductivity of the material and the measured thermal conductivity at the selected point in a table;
(h) training the neural network using the table; and in the measurement phase of using the neural network:
(i) obtaining a sample to be tested;
(j) selecting a point on the surface of the sample to be tested;
(k) determining a local topography around the point selected on the sample to be tested;
(l) measuring a thermal conductivity at the point selected on the sample to be tested using a thermal scanning probe microscope; and
(m) applying the local topography around the point selected on the sample to be tested and the measured thermal conductivity at the point selected on the sample to be tested to the neural network to deconvolute the effects of topography from thermal conductivity.

22. The method recited in claim 21, further comprising the step of repeating steps (d)-(h) for at least one additional selected point on the surface of the another sample.

23. The method recited in claim 21, further comprising the step of repeating steps (a)-(h) using at least one additional sample material.

24. The method recited in claim 22, further comprising the step of repeating steps (a)-(h) using at least one additional sample material.

25. The method recited in claim 21, wherein the local topographies determined in steps (e) and (k) use at least eight neighbor points to the selected points.

26. The method recited in claim 21, wherein the local topographies determined in steps (e) and (k) use less than eight neighbor points to the selected points.

27. A method for deconvoluting the effects of topography from a thermal conductivity measurement made by a thermal scanning probe microscope, comprising the steps of:
(a) selecting a point on the surface of a sample of a material for which the true thermal conductivity is known;
(b) determining a local topography around the selected point;
(c) measuring a thermal conductivity at the selected point using a thermal scanning probe microscope;
(d) using the local topography, the measured thermal conductivity and the true thermal conductivity to determine the effect of topography on the measured thermal conductivity;
(e) storing the determination of the effect of topography on the measured thermal conductivity;

(f) selecting a point on the surface of a sample of a test material;

(g) determining a local topography around the selected point on the surface of the sample of the test material;

(h) measuring a thermal conductivity at the selected point on the surface of the sample of the test material using a thermal scanning probe microscope; and (i) deconvoluting the effect of topography on the measured thermal conductivity at the selected point on the surface of the sample of the test material using the stored determination of the effect of topography on the measured thermal conductivity, the determined local topography around the selected point on the surface of the sample of the test material and the measured thermal conductivity at the selected point on the surface of the sample of the test material.

28. The method recited in claim 27, further comprising the step of measuring the true thermal conductivity.

29. The method recited in claim 28, further comprising the step of using an average thermal conductivity measured at one or more points in a substantially smooth portion of a surface of the sample as the true thermal conductivity.

30. The method recited in claim 27, further comprising the step of training a neural network to determine the effect of topography on the measured thermal conductivity.

31. The method recited in claim 27, further comprising the step of repeating steps (a)-(d) on a plurality of samples.

32. The method recited in claim 27, further comprising the step of repeating steps (f)-(i) for a plurality of points on the surface of the sample of the test material.

33. A system for deconvoluting the effects of topography from a thermal conductivity measurement, comprising the steps of:

means for selecting a point on the surface of a sample of a material having a true thermal conductivity;

means for determining a local topography around the selected point;

means for measuring a thermal conductivity at the selected point using a thermal scanning probe microscope;

means for using the local topography, the measured thermal conductivity and the true thermal conductivity to determine the effect of topography on the measured thermal conductivity;

means for storing the determination of the effect of topography on the measured thermal conductivity;

means for selecting a point on the surface of a sample of a test material;

means for determining a local topography around the selected point on the surface of the sample of the test material;

means for measuring a thermal conductivity at the selected point on the surface of the sample of the test material using a thermal scanning probe microscope; and means for deconvoluting the effect of topography on the measured thermal conductivity at the selected point on the surface of the sample of the test material using the stored determination of the effect of topography on the measured thermal conductivity, the determined local topography around the selected point on the surface of the sample of the test material and the measured thermal conductivity at the selected point on the surface of the sample of the test material.

34. The system of claim 33, further comprising means for measuring the true thermal conductivity.

35. The system of claim 34, further comprising means for using an average thermal conductivity measured at one or more points in a substantially smooth portion of a surface of the sample as the true thermal conductivity.

36. The system of claim 33, further comprising means for training a neural network to determine the effect of topography on the measured thermal conductivity.

* * * * *